(12) United States Patent
Shekalim

(10) Patent No.: US 8,050,729 B2
(45) Date of Patent: Nov. 1, 2011

(54) DEVICES FOR CONTINUOUS MEASUREMENT OF GLUCOSE IN BODY FLUID

(75) Inventor: Avraham Shekalim, Nesher (IL)

(73) Assignee: G-Sense Ltd., Tirat Hacarmel (IL)

( * ) Notice: Subject to any disclaimer, the term of this patent is extended or adjusted under 35 U.S.C. 154(b) by 1342 days.

(21) Appl. No.: 11/569,968

(22) PCT Filed: Jun. 28, 2005

(86) PCT No.: PCT/IL2005/000690
§ 371 (c)(1),
(2), (4) Date: Dec. 4, 2006

(87) PCT Pub. No.: WO2006/001024
PCT Pub. Date: Jan. 5, 2006

(65) Prior Publication Data
US 2008/0269584 A1    Oct. 30, 2008

(30) Foreign Application Priority Data
Jun. 28, 2004  (IL) .......................................... 162761

(51) Int. Cl.
*A61B 5/1455* (2006.01)
(52) U.S. Cl. ....................... 600/310; 600/322

(58) Field of Classification Search ................... 600/316, 600/310, 322
See application file for complete search history.

(56) References Cited

U.S. PATENT DOCUMENTS

| | | | |
|---|---|---|---|
| 4,008,717 A | | 2/1977 | Kowarski |
| 4,841,974 A | | 6/1989 | Gumbrecht et al. |
| 4,979,509 A | | 12/1990 | Hakky |
| 5,222,496 A | | 6/1993 | Clark et al. |
| 5,260,029 A | * | 11/1993 | Hosoi et al. ............. 422/82.08 |
| 5,944,660 A | | 8/1999 | Kimball et al. |
| 6,034,769 A | * | 3/2000 | Yufa ............................ 356/335 |
| 6,245,227 B1 | * | 6/2001 | Moon et al. .............. 210/198.2 |
| 6,312,393 B1 | * | 11/2001 | Abreu .......................... 600/558 |
| 6,618,603 B2 | | 9/2003 | Varalli et al. |
| 6,731,387 B2 | * | 5/2004 | Neimark et al. ............. 356/435 |
| 6,951,632 B2 | * | 10/2005 | Unger et al. ................. 422/505 |

* cited by examiner

*Primary Examiner* — Eric Winakur
(74) *Attorney, Agent, or Firm* — Mark M. Friedman

(57) ABSTRACT

A device for monitoring a constituent of body fluid continuously or repeatedly over a time period includes a body fluid sampling system and an optical sensor arrangement. The sampling system has a pumping arrangement which pumps body fluid from a cannula to a fluid sink. The optical sensor determines a concentration of at least one constituent of the body fluid. The pumping arrangement preferably ejects drops of body fluid from a fine nozzle. According to certain embodiments, optical sensor arrangements ensure that the optical paths do not pass through surfaces wetted by the fluid to be examined.

9 Claims, 8 Drawing Sheets

DEVICES FOR CONTINUOUS MEASUREMENT OF GLUCOSE IN BODY FLUID

FIELD AND BACKGROUND OF THE INVENTION

The present invention relates to continuous or near-continuous measurement of properties or constituents of body fluids, and particularly although not exclusively to measurement of blood glucose levels.

It is known to employ spectral analysis techniques to determine the concentration of constituents of the blood such as glucose concentrations. An example of such techniques is described in U.S. Pat. Nos. 5,222,496 and 4,979,509. Such systems generally operate through the skin, or are implanted. Systems which operate through the skin suffer from significant errors due to variations in properties of the skin not related to the constituents which are to be measured and due to relative movement between the sensor system and the skin and/or the underlying tissue.

Attempts at continuous, or near continuous, monitoring of blood glucose have been made for many years, as exemplified by U.S. Pat. Nos. 4,008,717 and 4,979,509. More recent attempts include U.S. Pat. No. 6,618,603.

There remains a need for a reliable, low-cost, disposable device which could provide minimally-invasive continuous or near-continuous monitoring of constituents of body fluids such as glucose.

SUMMARY OF THE INVENTION

The present invention is a device for continuous monitoring of one or more constituent of the blood or other body fluids, exemplified in the context of monitoring glucose levels in the blood.

According to the teachings of the present invention there is provided, a device for monitoring a constituent of body fluid continuously or repeatedly over a time period, the device comprising: (a) a body fluid sampling system including: (i) a cannula for defining a fluid path for withdrawing body fluid from the body, (ii) a fluid sink for storing a quantity of spent body fluid, and (iii) a pumping arrangement for generating a net flow of body fluid from the cannula to the fluid sink; and (b) an optical sensor arrangement associated with the body fluid sampling system and configured for determining a concentration of at least one constituent of the body fluid.

According to a further feature of the present invention, the pumping arrangement includes at least one cyclically actuated piezoelectric transducer deployed to generate the net flow of body fluid.

According to a further feature of the present invention, the pumping arrangement includes a nozzle arrangement for ejecting drops of the body fluid and a pulse generator for generating a pressure pulse within the body fluid so as to eject a drop from the nozzle arrangement.

According to a further feature of the present invention, there is also provided a pressure regulating valve for maintaining a pressure above atmospheric pressure in the fluid sink.

According to a further feature of the present invention, the nozzle arrangement is deployed so as to eject a drop from the nozzle arrangement towards a capillary uptake nozzle associated with the fluid sink.

According to a further feature of the present invention, the nozzle arrangement is deployed so as to eject a drop from the nozzle arrangement towards an absorbent medium included within the fluid sink.

According to a further feature of the present invention, the nozzle arrangement is deployed so as to eject a drop through a bubble tap arrangement.

According to a further feature of the present invention, the pulse generator is deployed so as to generate a pressure pulse through the body fluid within the cannula.

According to a further feature of the present invention, there is also provided a pressure wave augmenting configuration for augmenting a displacement of the pressure wave supplied to the cannula.

According to a further feature of the present invention, the optical sensor arrangement is deployed for determining the concentration of the at least one constituent in the body fluid making up the ejected drop while the ejected drop is in flight.

According to a her feature of the present invention, the optical sensor arrangement includes an illumination source for illuminating at least a portion of the body fluid along an illuminating optical path and a sensor element sensitive to at least one wavelength of radiation received from the portion of the body fluid along a sensing, optical path, and wherein the optical sensor arrangement is deployed such that at least one of the illuminating optical path and the sensing optical path does not pass through any surface which is wetted by the body fluid.

According to a her feature of the present invention, the optical sensor arrangement is deployed such that at least one of the illuminating optical path and the sensing optical path does not pass through any container wall.

According to a further feature of the present invention, the pumping arrangement includes a valveless pump configuration having: (a) a pumping chamber for containing a quantity of the body fluid; (b) a first directional flow impedance having a direction of minimum flow impedance from the cannula to the pumping chamber; (c) a second directional flow impedance having a direction of minimum flow impedance from the pumping chamber towards the fluid sink; and (d) a pulse generator for generating cyclic variations in volume of the pumping chamber, thereby generating the net flow of fluid.

According to a further feature of the present invention, there is also provided a nozzle in fluid communication with the second directional flow impedance such that operation of the valveless pump configuration causes growth of a droplet at the nozzle.

According to a further feature of the present invention, the optical sensor arrangement is configured to determine a concentration of the at least one constituent of the droplet at the nozzle.

According to a further feature of the present invention, the fluid sink includes a capillary medium deployed in predefined spatial relation to the nozzle such that, when the droplet grows to a predefined size, the droplet contacts the capillary medium and is drawn by capillary action into the fluid sink.

According to a further feature of the present invention, at least the cannula, the fluid sink and surfaces of the pumping arrangement coming in contact with the body fluid are implemented as part of a disposable cartridge, and wherein at least the optical sensor arrangement is implemented as part of a reusable housing configured for interchangeably receiving the disposable cartridge.

According to a further feature of the present invention, the reusable housing includes a body contact portion configured for temporary attachment to a body surface of a subject and a cover removably attachable to the body contact portion.

According to a further feature of the present invention, there is also provided a heating arrangement for locally heating at least part of the cannula.

According to a further feature of the present invention, the heating arrangement includes an electrical heating element associated with at least part of the cannula.

According to a flier feature of the present invention, the heating arrangement includes a laser directed towards at least part of the cannula.

According to a further feature of the present invention, the heating arrangement includes an actuator for generating vibration of at least part of the cannula.

There is also provided according to the teachings of the present invention, a device for monitoring a constituent of body fluid continuously or repeatedly over a time period, the device comprising: (a) a body fluid sampling system including: (i) a cannula for defining a fluid path for withdrawing body fluid from the body, (ii) a fluid sink for storing a quantity of spent body fluid, and (iii) a pumping arrangement for generating a net flow of body fluid from the cannula to the fluid sink; and (b) a sensor arrangement associated with the body fluid sampling system and configured for determining a concentration of at least one constituent of the body fluid, wherein the pumping arrangement includes a nozzle arrangement for ejecting drops of the body fluid and a pulse generator for generating a pressure pulse within the body fluid so as to eject a drop from the nozzle arrangement.

There is also provided according to the teachings of the present invention, a device for monitoring a constituent of body fluid continuously or repeatedly over a time period, the device comprising: (a) a body fluid sampling system including: (i) a cannula for deforming a fluid path for withdrawing body fluid from the body, (ii) a fluid sink for storing a quantity of spent body fluid, (iii) a pumping arrangement for generating a net flow of body fluid from the cannula to the fluid sink, and (iv) a pulse generator for generating a pressure pulse within the body fluid through the cannula; and (b) a sensor arrangement associated with the body fluid sampling system and configured for determining a concentration of at least one constituent of the body fluid.

According to a flirter feature of the present invention, there is also provided a pressure wave augmenting configuration for augmenting a displacement of the pressure wave supplied to the cannula.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a device for continuous monitoring of one or more constituent of the blood or other body fluids, exemplified in the context of monitoring glucose levels in the blood.

The principles and operation of devices according to the present invention may be better understood with reference to the drawings and the accompanying description.

By way of introduction, the present invention provides continuous or intermittent monitoring of one or more constituent of blood by sampling of body fluids at very low flow rates. According to a first particularly preferred set of implementations, in order to provide reliable control of very low flow rates, the device employs inkjet drop ejection technology in which a piezoelectric actuator fires micro-droplets from a nozzle. In an alternative preferred set of implementations, valveless pump technology based on directional fluid flow impedances is used. In either case, because of the minute quantities employed, the ejected drops over a period of hours up to as much as three days can be collected in a small internal storage volume typically of significantly less than one milliliter without requiring any external drainage.

In preferred implementations, optical sensing techniques such as those mentioned above are used. One problem associated with the use of optical sensing techniques for analysis of fluid within a conduit or container is that layers of the fluid adjacent to the surfaces of the conduit or container tend not to move, and are therefore not representative of the bulk properties of the new fluid which has most recently been drawn into the device, thereby giving rise to inaccuracies in measurements. To address this issue, it is a particular feature of certain preferred implementations of the invention that some or all of the optical paths between the optical sensors and the body fluid are arranged to avoid passing through surfaces which are wetted by the fluid. These and other features of the present invention will become clearer from the following specific examples.

Figure 1A:
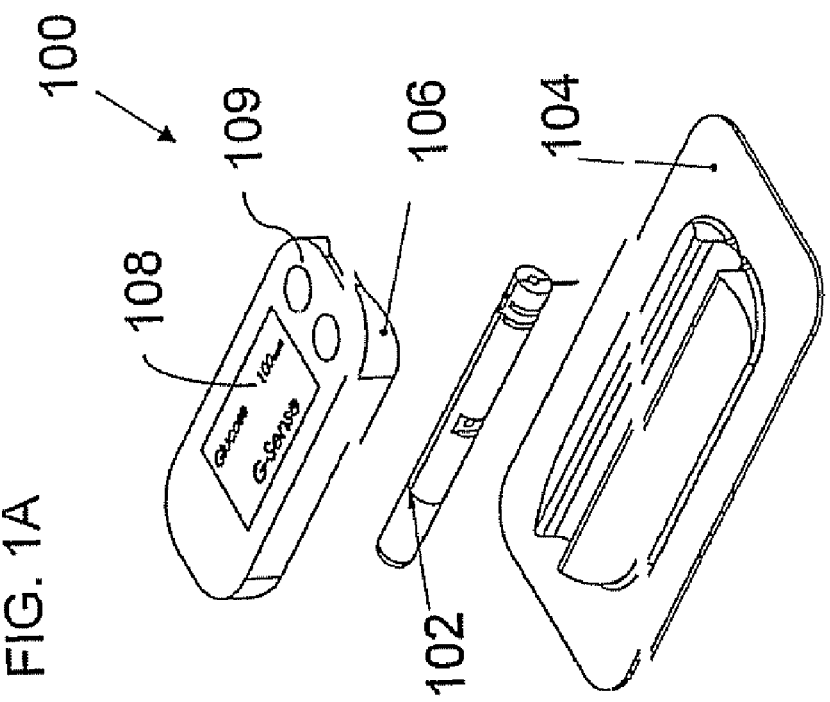
FIGS. 1A and 1B are disassembled and assembled isometric views respectively, of a device for continuous measurement of glucose levels in the blood, constructed and operative according to the teachings of the present invention.
Figure 1B:
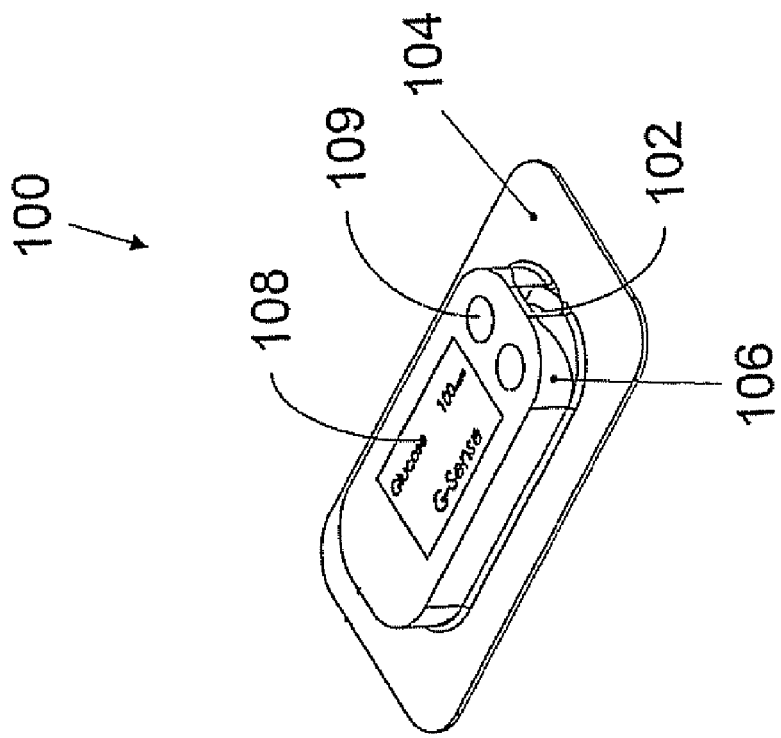

Turning now to the drawings, FIGS. 1A and 1B show a device, generally designated 100, for monitoring a constituent of body fluid continuously or repeatedly over a time period. In a particularly preferred non-limiting implementation as illustrated here, device 100 is implemented with a first set of components formed as a disposable cartridge 102 which is exchangeably received by a reusable housing which houses other, reusable components of the device. In the preferred implementation illustrated here, the reusable housing includes a body contact portion 104 configured for temporary attachment to a body surface of a subject, for example by use of suitable adhesives as is known in the art, and a cover 106 removably attachable to the body contact portion. Preferably, cover 106 includes the majority of the more costly components of the device, and in particular, the majority of the components which do not come into direct contact with body fluids. These typically include a display 108, control buttons 109 and various other components not visible here such as a power supply, an electronic control system, an alarm and a wired communication interface or wireless transmitter for data transfer to a remote device. The subsequent FIGS. 2-6 describe in greater detail the structure and operation of various implementations of disposable cartridge 102. The corresponding structure and function of an implementation of the reusable housing suited to the features of each implementation will be self-evident to one ordinarily skilled in the art.

Figure 2:
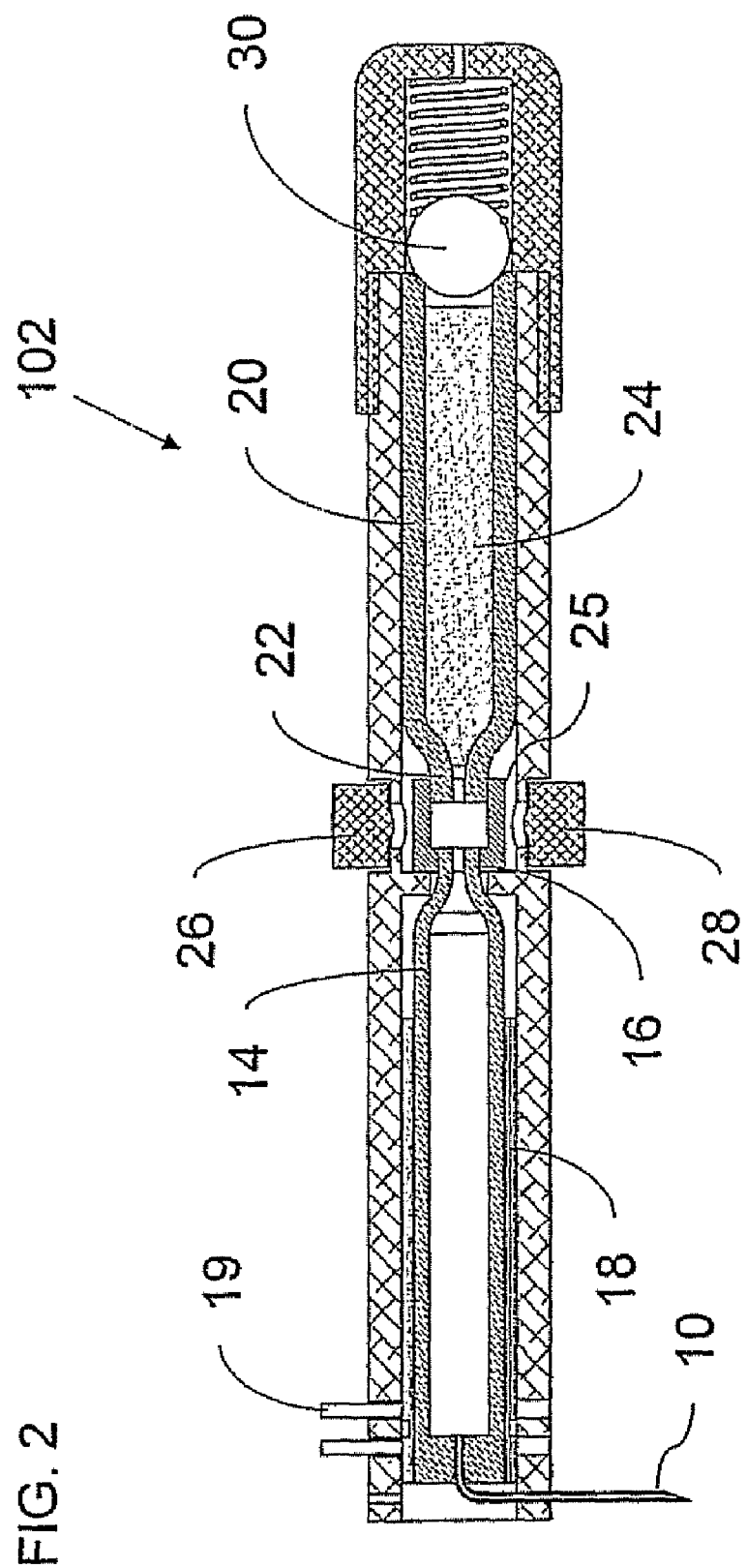
FIG. 2 is a schematic cross-sectional view (not to scale) taken axially through a first implementation of a disposable cartridge for use in the device of FIGS. 1A and 1B.

Turning now to a first example of a disposable cartridge 102 shown in FIG. 2, this includes a cannula 10 in fluid connection with a first chamber 14. Cannula 10 may be implemented as any conduit (or number of conduits) while is suitable for insertion into or trough the skin of a subject. Examples include, but are not limited to, a metal needle as shown, a flexible Teflon tube, and various hollow microneedle structures. First chamber 14 is here implemented as a length of capillary tube, preferably with an internal diameter of less than 1 mm, and more preferably between 0.3-0.5 mm and most preferably about 0.3 mm. This relatively small cross-section ensures that the body fluids in the capillary are replaced rapidly, even at very low flow rates, so that the fluid content of the first chamber represents accurately the current composition of the fluids within the body from which they were withdrawn with minimum time lag. The capillary tube is formed with a narrow nozzle 16 which has an internal diameter at its end of 10-150 μm. About the capillary tube is deployed a cylindrical piezoelectric actuator 18 for generating pressure pulses within capillary tube 14 so as to eject droplets from nozzle 16. Piezoelectric actuator 18 has projecting contacts 19 which are deployed to mate with corresponding contacts of actuator driving circuitry located within cover 106.

Facing nozzle 16 is a second capillary tube 20 with an uptake nozzle 22 which tales up the droplets by capillary action. Capillary tube 20 is typically of larger internal diameter than fist chamber 14 since its primary function is to provide a fluid sink for receiving and storing spent body fluid, i.e., body fluid which is no longer required for measurements. Capillary tube 20 is preferably partially or completely filled with an absorbent medium such as open-cell sponge material 24 which serves to soak-up the droplets and helps to prevent leakage. Sponge material 24 may optionally extend beyond capillary tube 20.

A bubble trap 25 is deployed around and between nozzle 16 and uptake nozzle 22 to maintain an air bubble adjacent to nozzle 16 to facilitate drop ejection.

An optical sensor, including all optical transmitter (illumination source) 26 and a receiver (sensor element) 28 are deployed for performing the required monitoring of the body fluids. The components are preferably reusable components which are mounted on the reusable housing in such a manner as to be correctly deployed (as shown) relative to the disposable cartridge when assembled. The exact nature of the sensor is chosen according to the type of measurements to be performed according to techniques well know in the art and exemplified by the aforementioned U.S. Pat. Nos. 5,222,496 and 4,979,509.

A pressure regulating valve 30 is preferably configured to maintain a pressure slightly above atmospheric pressure to provide the slight back-pressure differential for proper operation of the drop ejection mechanism, as is well known in the field of inkjet technology. Excess pressure is released to the atmosphere without release of any body fluids, since the body fluids are retained within the absorbent material. Optionally, a waterproof gas permeable membrane (not shown) may be added to ensure no leakage of body fluids.

As mentioned above, the device also includes additional components not shown here, which are typically deployed as part of the reusable housing. These typically include a battery power supply, electronics for driving the piezoelectric actuator, electronics for driving the optical sensor and processing its output and an output arrangement for directly displaying measurement results and/or for outputting results to an external local or remote system. The aforementioned electronics may be implemented separately or in combination, and may employ dedicated electronic arrangements, suitably programmed general-purpose processor unit(s) or firmware. Preferred implementations also include at least one error indicator for providing an alarm in one or more malfunction condition.

This implementation also illustrates one particularly preferred aspect of the present invention with regard to positioning of the optical sensor components. Specifically, it is a particularly preferred feature according to one aspect of the present invention that an illuminating optical path from illumination source 26 to an illuminated portion of the body fluid and/or a sensing optical path from the illuminated portion of the body fluid to sensor element 28 do not pass through any surface which is wetted by the body fluid. Thus, in the implementation of FIG. 1, measurements are performed by directing a pulse of illumination at droplets in flight. Since the drop emission occurs at a clearly predefined time relative to the piezoelectric actuator pulse and the drop size and speed are very consistent, highly accurate synchronization can readily be achieved between drop ejection and operation of the optical sensor. The use of free-flying drops for the optical measurements ensures consistent optical conditions since it is unaffected by accumulation of surface layers of fluid on the internal surfaces of the capillary tubes.

Prior to use, disposable cartridge is primed by filling first chamber 14 with a biocompatible fluid such as saline solution. This may be done immediately prior to use simply by use of a syringe suitably mated with cannula 10, or alternatively during manufacture of the device prior to assembly. Optionally, a quantity of air or, other gas may first be injected into the device to ensure the desired back-pressure for correct operation of the drop ejection arrangement. In order to ensure that the bubble trap 25 is clear of liquid, a reverse pressure (suction) may be applied by withdrawing a plunger of the filling syringe until significant resistance is felt. This indicates that the fluid level is at nozzle 16 resulting in strong capillary forces which act against further withdrawal of the liquid.

In operation, the device is positioned with the cannula inserted subcutaneously or into a minor vein and the piezoelectric actuator 18 is actuated to start ejecting drops from nozzle 16 towards uptake nozzle 22 where they are taken up into the fluid sink. Initially, the electronic control actuates the system to eject a number of drops (for example, around 200) sufficient to replace the original priming fluid within first chamber 14 with interstitial fluid or blood drawn through cannula 10. Additionally, or alternatively, completion of the initial sampling cycle can be identified by stabilization of the values of the body fluid constituent to be monitored as measured by the optical measurement system. Once initial sampling is complete, the drop ejection from nozzle 16 is reduced to that required for the rate of sampling and volume flow rate desired, and monitoring of the constituent of interest proceeds according to programmed and/or selected parameters.

Parenthetically, it should be noted that the pressure pulses from piezoelectric actuator 18 also propagate along cannula 10 back into the body of the subject. Unlike nozzle 16, the tip of cannula 10 is immersed in body fluids so that no drop ejection or net fluid flow results from the momentary pressure pulses. These pulses are however of importance since they are sufficient to dislodge any tissue which might otherwise become lodged in the opening of the cannula and cause a flow blockage.

Figure 3:
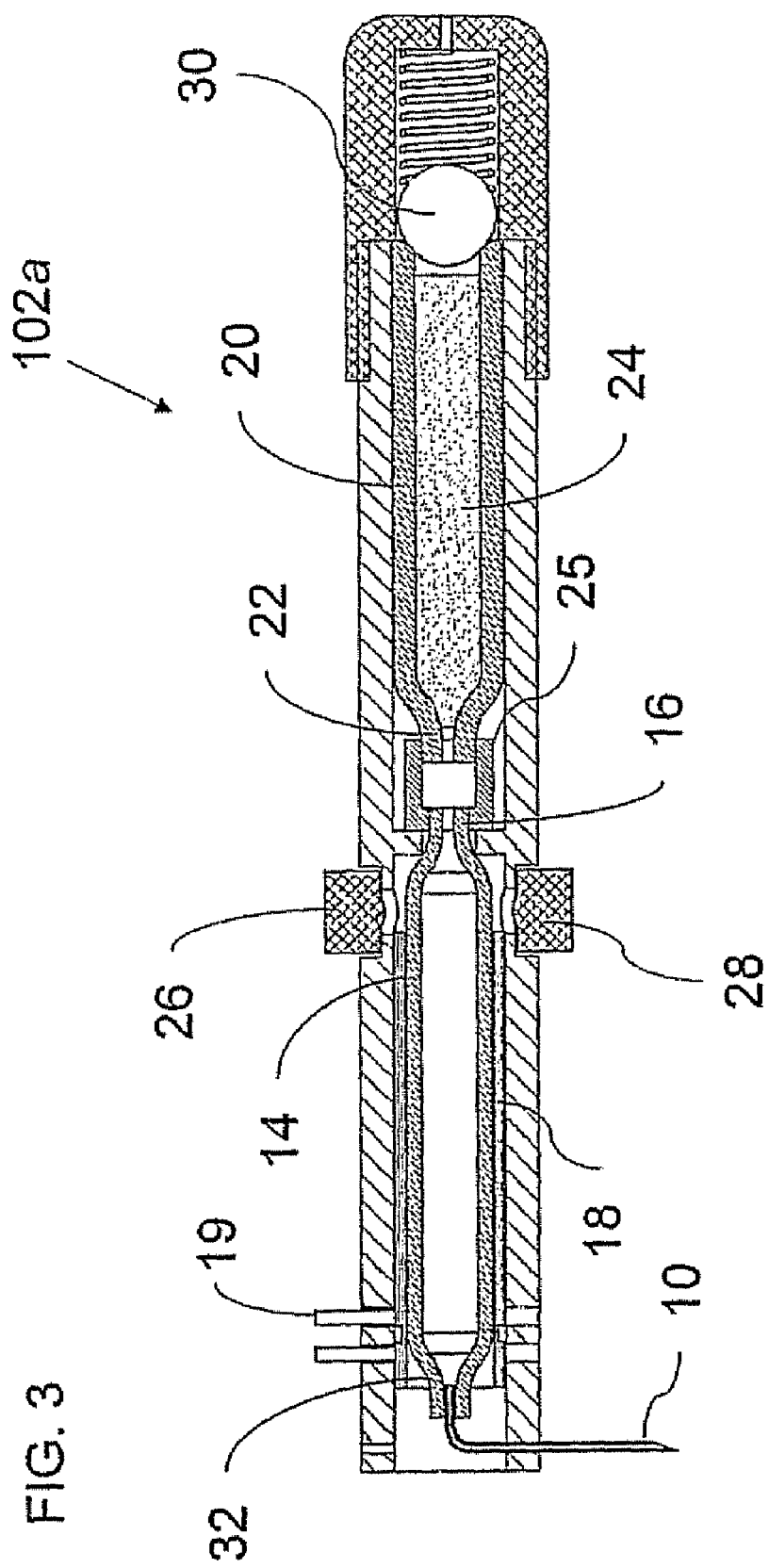
FIG. 3 is a schematic cross-sectional view (not to scale) taken axially through a second implementation of a disposable cartridge for use in a device similar to the device of FIGS. 1A and 1B.

Turning now to FIG. 3, Ns shows a variant implementation of disposable cartridge 102, here designated 102a. The structure and function of disposable cartridge 102a closely parallels that of FIG. 2, and equivalent elements are similarly labeled. Disposable cartridge 102a differs from the previous implementation primarily in that first chamber 14 is here formed with a pressure wave augmenting configuration 32 for augmenting a displacement of the pressure waves supplied to cannula 10. Pressure wave augmenting configuration 32 is preferably implemented as a part of first chamber 14 which has a gradually reducing cross-section, in a manner similar to nozzle 16, and connects at its narrow end to cannula 10. This structure enhances the aforementioned unblocking effect of the reverse-direction part of the pressure pulses generated by actuator 18, thereby freeing cannula 10 from any obstruction.

Parenthetically, FIG. 3 also illustrates an alternative positioning of the components 26 and 28 of the optical measurement system for measuring die concentration of the constituent of interest directly through the walls of first chamber 14. Although the sensor configuration of FIG. 2 is believed to have significant advantages in many cases, other options such as the location shown here also fall within the broad scope of the present invention. Parenthetically, it should also be noted that, depending upon the exact optical sensing technology used, the components of the optical sensing system may be deployed in various different relative geometrical arrangements, for example, with the illumination source and sensor element both located on the same side of the target volume of fluid Examples of such geometrical arrangements will be illustrated below with reference to FIGS. 5 and 6.

Figure 4:
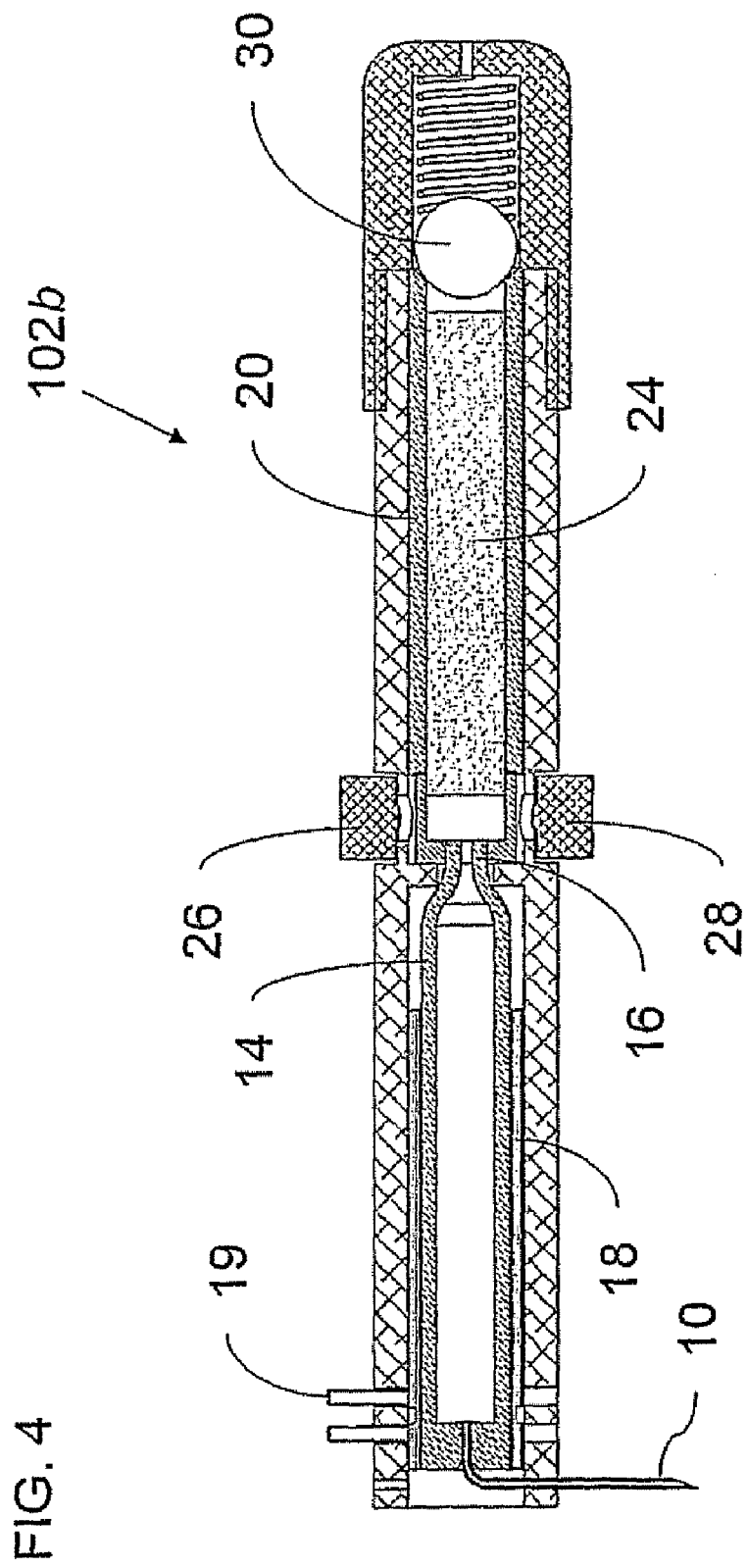
FIG. 4 is a schematic cross-sectional view (not to scale) taken axially through a third implementation of a disposable cartridge for use in the device of FIGS. 1A and 1B.

Turning now to FIG. 4, this shows a second variant implementation of disposable cartridge 102, here designated 102b. The structure and function of disposable cartridge 102b closely parallels that of FIG. 2, and equivalent elements are similarly labeled. Disposable cartridge 102b differs from cartridge 102 in that uptake nozzle 22 and bubble trap 25 are omitted. In his case, the droplets fall directly onto sponge material 24 and are absorbed. The leading surface of the sponge may be pre-moistened or otherwise pre-treated in order to reduce the risk of splash-back at the onset of operation. In all other respects, the device of FIG. 4 is structurally and functionally equivalent to that of FIG. 2.

Figure 5:
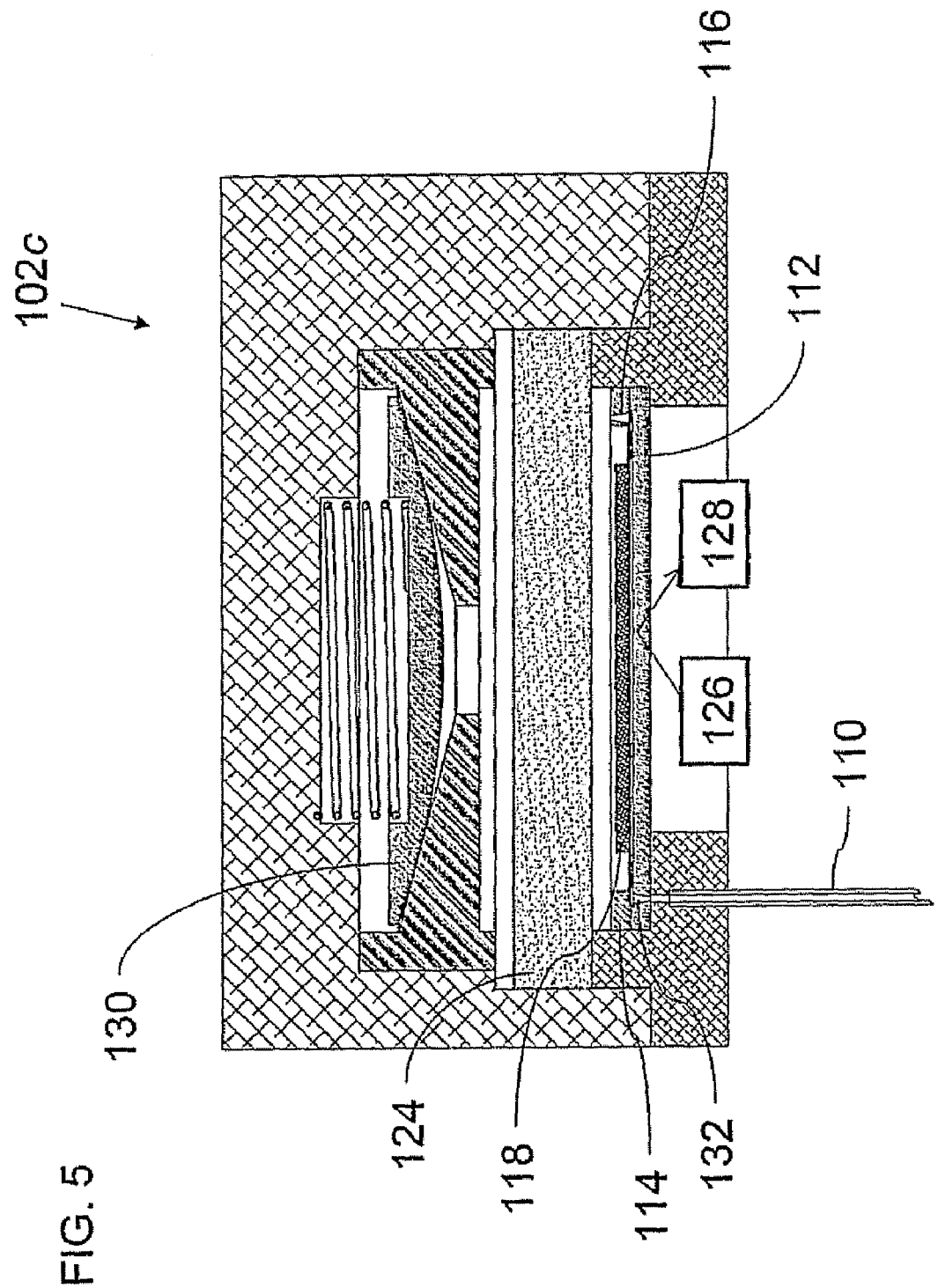
FIG. 5 is a schematic cross-sectional view (not to scale) taken axially through a disposable cartridge for use in an alternative embodiment of the device of FIGS. 1A and 1B.

The implementations of the present invention illustrated thus far are based upon an elongated, roughly cylindrical cartridge structure. It should be appreciated, however, that the principles of the present invention may be applied to devices with many different geometrical structures. By way of one non-limiting example, FIG. 5 illustrates a flirter implementation of a replaceable cartridge, generally designated 102c, which employs a short and flat cylindrical "button" type profile to perform functions similar to the previous embodiments.

In this case, disposable cartridge 102c has a cannula 110 in fluid connection with a first chamber defined a lower glass table 112 and an upper relatively thin glass diaphragm 114. In this example, the connection of cannula 110 to the first chamber is via a pressure pulse augmentation configuration 132, functionally analogous to augmentation configuration 32 of FIG. 3. At the other side of the first chamber (on the right as illustrated here) is a nozzle 116. A planar piezoelectric actuator 118 is associated with glass diaphragm 114 such that on actuation of the actuator, the diaphragm flexes downwards and reduces the volume of the first chamber, thereby ejecting a droplet from nozzle 116. Opposite the nozzle is a block of absorbent material 124, functionally analogous to the exposed surface of sponge 24 in FIG. 4. Above absorbent material 124 is a pressure regulating valve 130 which maintains the required back pressure at nozzle 116. For optical sensing of the concentration of the constituent of interest in body fluid within the first chamber, al illumination source 126 and a sensor element 128, here too preferably associated with a reusable housing (not shown), are located beneath glass table 112.

Figure 6:
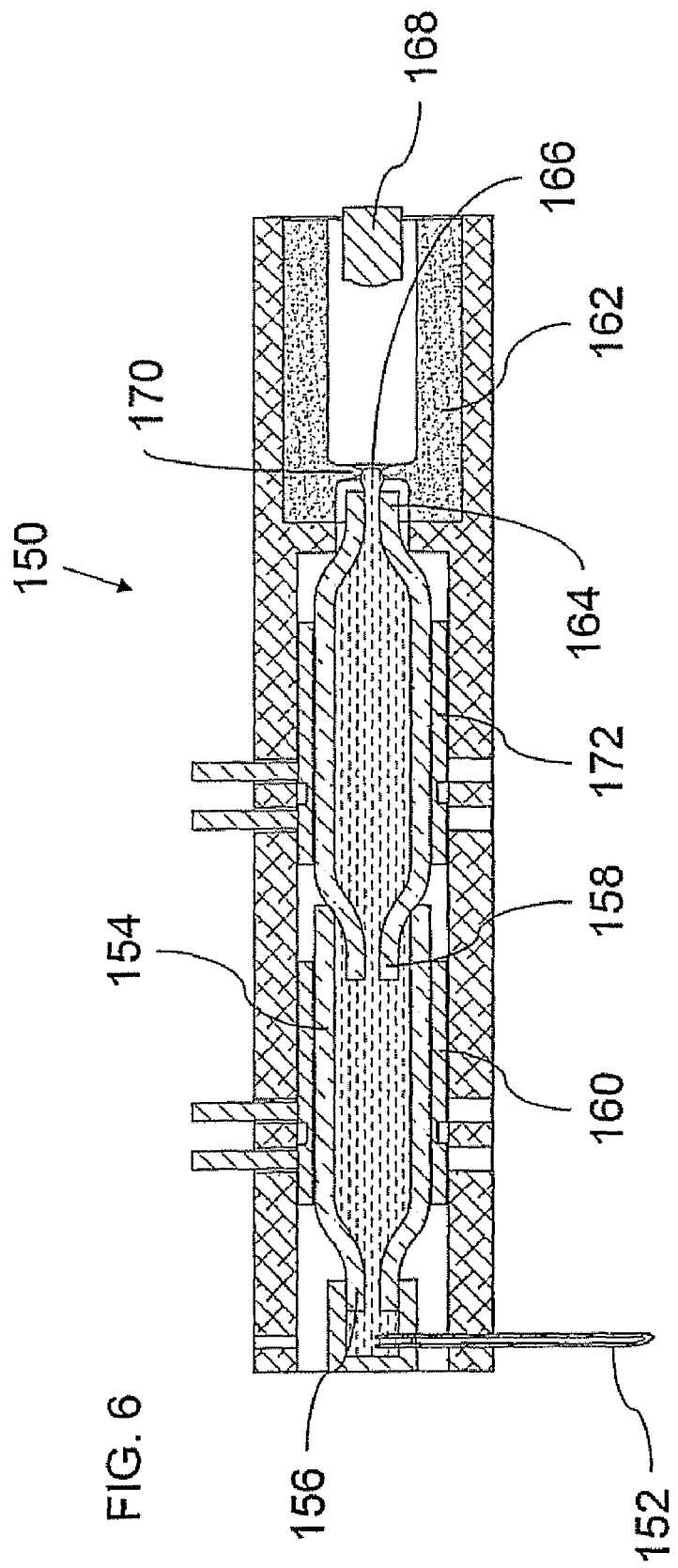
FIG. 6 is a schematic cross-sectional view (not to scale) taken axially through a disposable cartridge for use in a further alternative embodiment of a device similar to the device of FIGS. 1A and 1B.

Turning now to FIG. 6, this illustrates an alternative embodiment of the present invention which is based on a different pumping technique. Unlike the ink-jet type mechanism of the embodiment previously described, the cartridge of FIG. 6 is based upon a valveless pump concept through which directional flow restrictions on either side of a variable volume pumping chamber generate a net fluid flow as the pumping chamber volume oscillates.

Thus, FIG. 6 shows a disposable cartridge, generally designated 150, for use in a device similar to device 10 of FIGS. 1A and 1B. In this case, cartridge 150 includes a cannula 152 in fluid communication (directly or indirectly) with a valveless pump configuration including a pumping chamber 154 for containing a quantity of the body fluid, a first directional flow impedance 156 having a direction of minimum flow impedance from the cannula to the pumping chamber, and a second directional flow impedance 158 having a direction of minimum flow impedance from the pumping, chamber towards the fluid sink. A pulse generator 160, typically implemented as a cylindrical piezoelectric actuator similar to that used in the previous embodiments, is deployed for generating cyclic variations in volume of the pumping chamber, thereby generating a net flow of fluid to a fluid sink 162 in the form of a body of absorbent material. Cartridge 150 preferably also features a nozzle 164 in fluid communication with directional flow impedance 158 such that operation of the valveless pump configuration causes growth of a droplet 166 at the nozzle.

Various configurations may be employed to provide the directional flow impedances 156 and 158. In the example illustrated here, roughly conical restrictions function in one direction as a nozzle which throttles-down flow whole, in the reverse direction, they function as a diffuser with relatively lower flow impedance. It will be appreciated that other directional (i.e., directionally asymmetric) flow restrictions may also be used.

Unlike the previous embodiment based upon drop ejection, this embodiment incrementally "grows" a droplet attached to nozzle 164. In certain preferred implementations of the present intention, this exposed droplet 166 and/or the fluid behind the droplet within nozzle 164 itself is the fluid used by an optical sensor arrangement 168 to determine the concentration of the at least one constituent of the droplet at the nozzle. To this end, optical sensor arrangement 168 preferably includes both an illumination source and a sensor element combined into a single axially-directed sensor structure aligned with the opening of nozzle 164. In this manner, neither the illuminating optical path nor the sensing optical path passes through any container wall, thereby avoiding any and all inaccuracies and calibration variations which result from the properties of the container walls and fluid or dirt collected on their surfaces.

The incremental growth of a droplet at nozzle 164 requires an appropriate uptake arrangement to ensure that the droplet reaches fluid sink 162 without splashing optical sensor arrangement 168 or dripping on other sensitive areas. According to a particularly preferred feature of this embodiment of the present invention, the fluid sink includes a capillary medium, in this case an extension of absorbent medium 162, which is deployed in predefined spatial relation to nozzle 164 such that, when droplet 166 grows to a predefined size, the droplet contacts the capillary medium and is drawn by capillary action into fluid sink 162. In the implementation shown here, the capillary medium is implemented as radially inward projecting fingers, or an annular collar 170, attached to or integrally formed with absorbent medium 162 so as to remain at the aforementioned spatial relation to nozzle 164 without obscuring the optical illumination and sensing paths of optical sensor arrangement 168.

Optionally, the pressure pulses generated by actuator 160 in the direction of cannula 152 may be enhanced by use of an additional piezoelectric actuator 172 deployed on the conduit between flow impedance 158 and nozzle 164. Actuator 172 is operated intermittently, i.e., less frequently than actuator 160, and may advantageously be synchronized at the same moment as a pulse of actuator 160 so as to generate a combined blockage-clearing pressure pulse along cannula 152. In the absence of back-pressure at nozzle 164 (since this embodiment does not employ a pressure regulating valve), the pressure pulse does not result in ejection of a droplet as in the previous embodiments.

Finally, turning to FIGS. 7A-7D, reference is made to a further optional but preferred feature which may be combined with any of the implementations discussed above. Specifically, it has been found that localized heating of tissue around an inserted cannula is, in many cases, effective to increase the fluid content of the surrounding tissue, and hence to facilitate withdrawal of the body fluids through the cannula for analysis. Accordingly, the present invention provides a number of heating arrangements for locally heating at least part of the cannula 180.

Figure 7A:
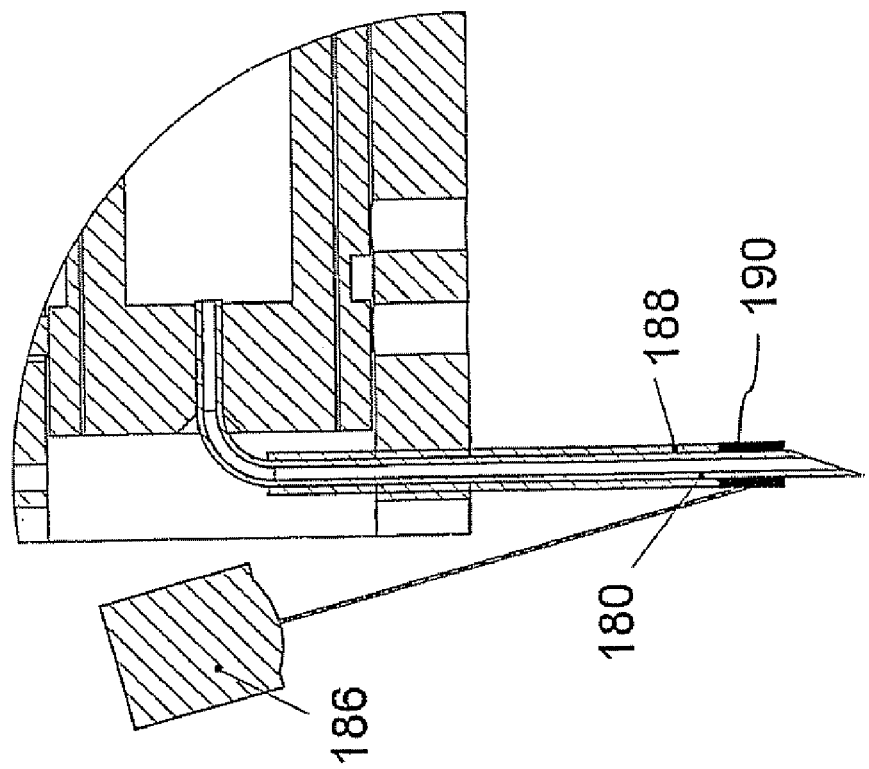
FIGS. 7A-7D illustrate schematically four alternative implementations of a heating arrangement for heating, at least part of a cannula in any of the aforementioned embodiments.

Referring first to FIG. 7A, this illustrates a first implementation of a heating arrangement in which an electrical heating element 182 is directly associated with at least part of cannula 180. In the example illustrated here, heating element 182 is incorporated into a Teflon sleeve 184 which overlies a major portion of cannula 180.

Figure 7B:
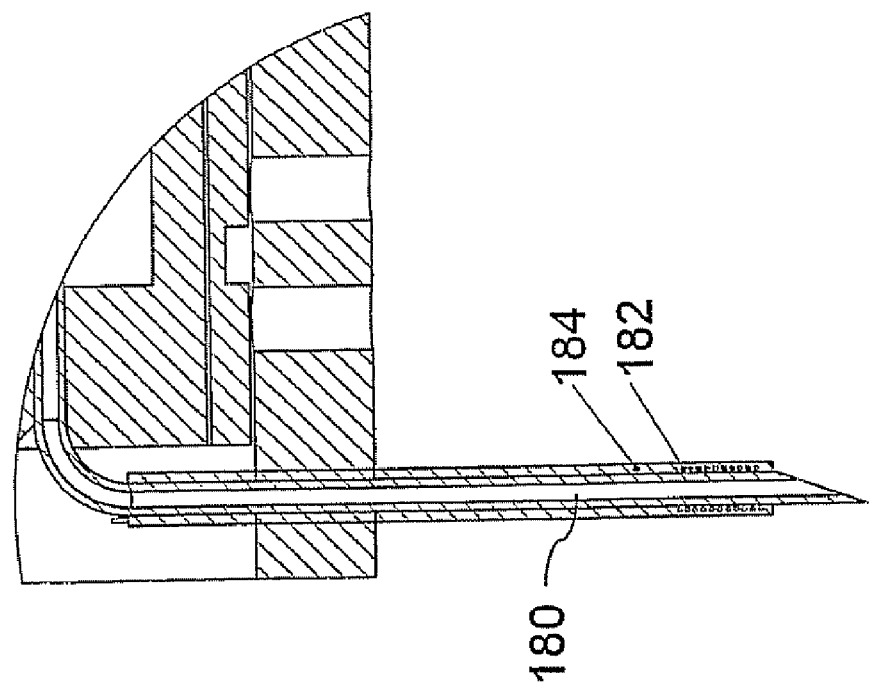

FIG. 7B shows a further option for a heating arrangement in which a laser 186 is directed towards at least part of the cannula. In order to enhance localized absorption of the laser radiation, cannula 180 is preferably provided with a complementary absorptive region. This is conveniently achieved by using a Teflon sleeve 188 which has a region 190 treated by addition of, or coating by, absorptive material.

Figure 7C:
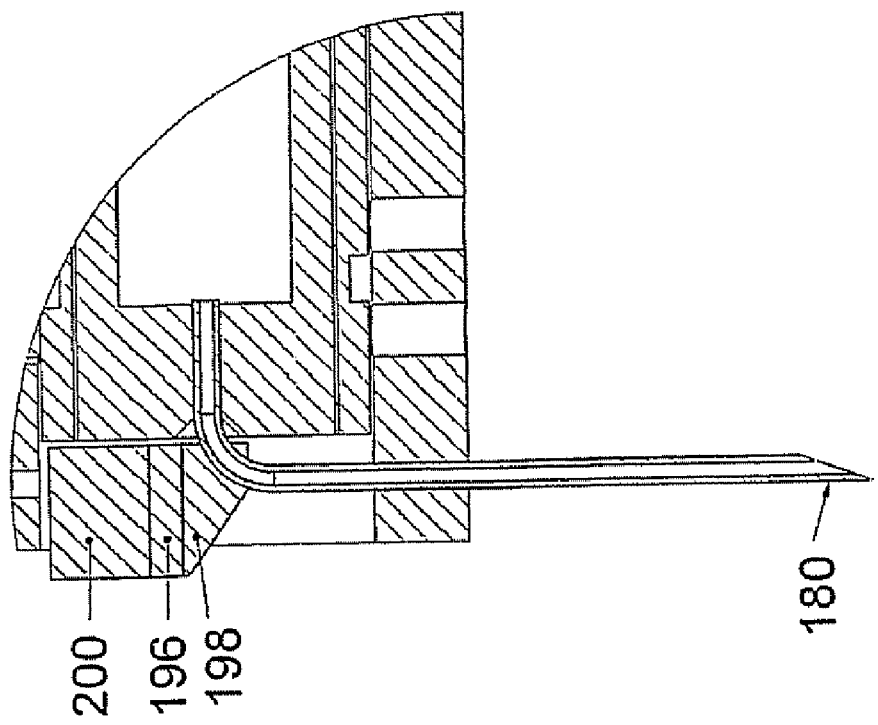
Figure 7D:
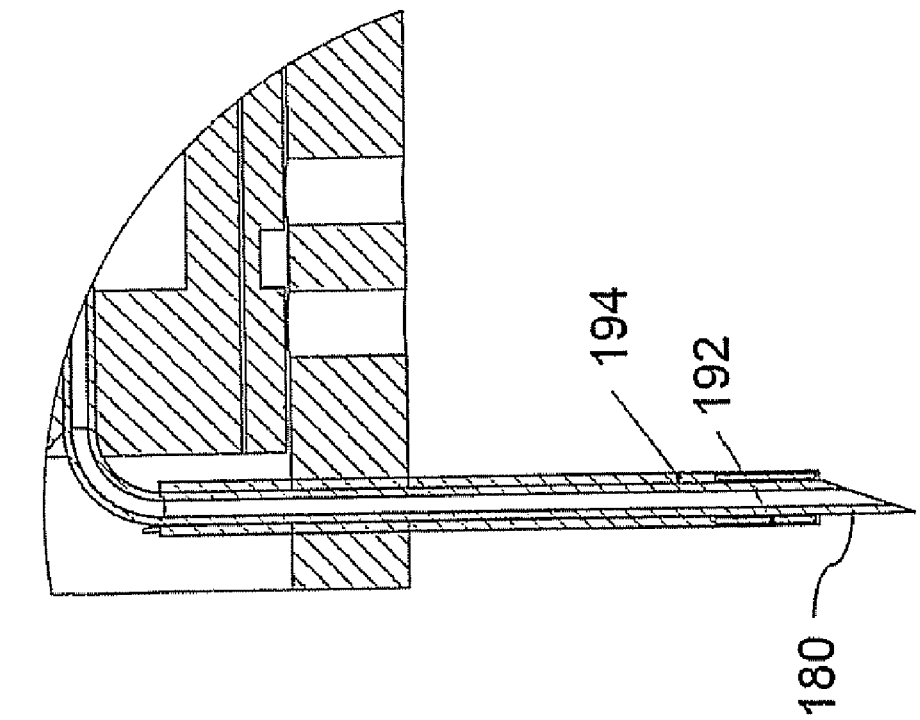

FIGS. 7C and 7D illustrate a further approach to heating of cannula 180 by use of vibrations. Specifically, an actuator is deployed to generate vibration of at least part of the cannula, which then becomes heated through various effects including frictional contact with the surrounding body tissue. In the case of FIG. 7C, vibrations are generated by a cylindrical piezoelectric actuator element 192 deployed around the cannula itself and secured by attachment to a Teflon sleeve 194. In the case of FIG. 7D, a piezoelectric actuator 196 is deployed at the upper end of cannula 180 within the cartridge itself Piezoelectric actuator 196 is connected to the cannula through a mechanical adapter 198, and a counterweight 200 provides sufficient inertia on the opposite side of the actuator to ensure effective vibration.

It will be appreciated that the above descriptions are intended only to serve as examples, and that many other embodiments are possible within the scope of the present invention as defined in the appended claims.

What is claimed is:

1. A device for monitoring, continuously or repeatedly over a time period, a concentration of an analyte extracted from within a body, the device comprising:
   (a) a fluid transfer system adapted to generate of flow of a fluid containing at least one analyte, the flow passing from the body to a sensing location; and
   (b) an optical sensor arrangement associated with said fluid transfer system and configured for determining the concentration of the at least one analyte at said sensing location,
   wherein said optical sensor arrangement includes an illumination source for illuminating at least a portion of the fluid along an illuminating optical path and a sensor element sensitive to at least one wavelength of radiation received from said portion of the fluid along a sensing optical path, and wherein said optical sensor arrangement is deployed such that at least one of said illuminating optical path and said sensing optical path does not pass through any surface which is wetted by the fluid.

2. The device of claim 1, wherein said optical sensor arrangement is deployed such that at least one of said illuminating optical path and said sensing optical path does not pass through any container wall.

3. The device of claim 1, wherein said fluid transfer system includes at least one cyclically actuated piezoelectric transducer deployed to generate a net flow of the fluid.

4. The device of claim 1, wherein said fluid transfer system includes a nozzle arrangement for ejecting drops of the fluid and a pulse generator for generating a pressure pulse within the fluid so as to eject a drop from said nozzle arrangement.

5. The device of claim 4, further comprising a pressure regulating valve for maintaining a pressure above atmospheric pressure in a fluid sink deployed for receiving the ejected drops.

6. The device of claim 4, wherein said nozzle arrangement is deployed so as to eject a drop from said nozzle arrangement towards a capillary uptake nozzle.

7. The device of claim 4, wherein said nozzle arrangement is deployed so as to eject a drop from said nozzle arrangement towards an absorbent medium.

8. The device of claim 4, wherein said nozzle arrangement is deployed so as to eject a drop through a bubble trap arrangement.

9. The device of claim 4, wherein said optical sensor arrangement is deployed for determining the concentration of the analyte in the fluid making up said ejected drop while said ejected drop is in flight.

* * * * *